(12) United States Patent
Zunker

(10) Patent No.: US 6,770,025 B2
(45) Date of Patent: Aug. 3, 2004

(54) MOLAR SHAPED VAGINAL INCONTINENCE INSERT

(75) Inventor: MaryAnn Zunker, Oshkosh, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 3 days.

(21) Appl. No.: 10/245,964

(22) Filed: Sep. 18, 2002

(65) Prior Publication Data

US 2004/0054252 A1 Mar. 18, 2004

(51) Int. Cl.[7] ................................................. A61F 2/00
(52) U.S. Cl. ...................................................... 600/29
(58) Field of Search ............... 600/29–32; 128/DIG. 25, 128/885, 830, 841; 604/385.1, 11–18

(56) References Cited

U.S. PATENT DOCUMENTS

| 1,280,979 A | 10/1918 | Ellis |
| 1,790,801 A | 2/1931 | Dickstein |

(List continued on next page.)

FOREIGN PATENT DOCUMENTS

| BR | PI 9302334-0 A | 7/1995 |
| DE | 1815375 | 9/1970 |
| DE | 2747245 | 4/1979 |
| DE | 3122954 A1 | 1/1983 |
| DE | 3720858 A1 | 1/1989 |
| DE | 19602878 C1 | 1/1996 |
| EP | 0460807 A2 | 12/1991 |
| EP | 0264258 B1 | 4/1992 |
| EP | 0498912 A1 | 8/1992 |
| EP | 0663197 A1 | 7/1995 |
| EP | 0363421 B2 | 10/1995 |
| EP | 0714271 B1 | 6/1996 |
| FR | 2228464 | 12/1974 |
| FR | 2342717 | 9/1977 |
| GB | 1115727 | 5/1968 |
| GB | 1116742 | 6/1968 |
| GB | 1359343 | 7/1974 |
| WO | WO 88/10106 | 12/1988 |
| WO | WO 94/13223 | 6/1994 |
| WO | WO 95/05790 | 3/1995 |
| WO | WO 95/16423 | 6/1995 |
| WO | WO 95/28139 | 10/1995 |

(List continued on next page.)

OTHER PUBLICATIONS

U.S. patent application Ser. No. 09/675,459 filed Sep. 28, 2000, entitled "Urinary Incontinence Device and Method of Making Same" pp. 1–24.
U.S. patent application Ser. No. 09/675,460 filed Sep. 28, 2000, entitled "Resilient Incontinence Insert and a Method of Making the Same", pp. 1–29.
U.S. patent application Ser. No. 10/039,230 filed Dec. 31, 2001, entitled "Incontinence Insert Device and Method of Using Same", pp. 1–18.
U.S. patent application Ser. No. 10/246,005 filed Sep. 18, 2002, entitled "C–Shaped Vaginal Incontinence Insert", pp. 1–15.
U.S. patent application Ser. No. 10/328,428 filed Dec. 23, 2002, entitled "Compressible Resilient Incontinence Insert", pp. 1–16.
Concert Fabricatation. Ltee, *Nonwovens Industry*, p. 1110, May, 1996.

Primary Examiner—Samuel G. Gilbert
(74) Attorney, Agent, or Firm—Brinks Hofer Gilson & Lione; G. Peter Nichols

(57) ABSTRACT

A molar shaped urinary incontinence device is disclosed. The device is a flexible molar shaped insert having a cross-sectional area at the top that is larger than the cross-sectional area of the bottom. The top respectively contacts at least two opposed vaginal walls. A channel may be provided to connect an aperture on the top surface and an aperture on the bottom surface to allow normal discharge of secretions. A removal member may be provided on the device such that when the removal member is pulled in a direction away from the device, the top collapses upon itself.

17 Claims, 3 Drawing Sheets

U.S. PATENT DOCUMENTS

| | | |
|---|---|---|
| 2,057,206 A | 10/1936 | Pohl |
| 2,092,427 A | 9/1937 | Ross |
| 2,201,412 A | 5/1940 | Stein |
| 2,264,586 A | 12/1941 | Ross |
| 2,298,752 A | 10/1942 | Crockford |
| 2,355,628 A | 8/1944 | Calhoun |
| 2,401,585 A | 6/1946 | Seidler |
| 2,487,200 A | 11/1949 | Trager |
| 2,491,017 A | 12/1949 | Robinson |
| 2,501,972 A | 3/1950 | Seidler |
| 2,519,912 A | 8/1950 | Laun |
| 2,700,188 A | 1/1955 | Buresh et al. |
| 2,711,173 A | 6/1955 | Seidler |
| 2,739,593 A | 3/1956 | McLaughlin |
| 2,890,497 A | 6/1959 | Langdon et al. |
| 2,938,519 A | 5/1960 | Marco |
| 3,011,495 A | 12/1961 | Brecht |
| 3,032,036 A | 5/1962 | Rader et al. |
| 3,034,508 A | 5/1962 | Nalle, Jr. |
| 3,079,921 A | 3/1963 | Brecht et al. |
| 3,090,385 A | 5/1963 | Brecht |
| 3,138,159 A | 6/1964 | Schmidt |
| 3,369,159 A | 2/1968 | Crockford |
| 3,409,011 A | 11/1968 | Mittag |
| 3,452,752 A | 7/1969 | Crescenzo |
| 3,469,286 A | 9/1969 | Crockford |
| 3,543,754 A | 12/1970 | Jones, Sr. |
| 3,554,184 A | 1/1971 | Habib |
| 3,596,328 A | 8/1971 | Voss |
| 3,643,661 A | 2/1972 | Crockford |
| 3,644,078 A | 2/1972 | Tachibana et al. |
| 3,646,929 A | 3/1972 | Bonnar |
| 3,705,575 A | 12/1972 | Edwards |
| 3,706,311 A | 12/1972 | Kokx et al. |
| 3,762,413 A | 10/1973 | Hanke |
| 3,765,417 A | 10/1973 | Crockford |
| 3,799,165 A | 3/1974 | Wennerblom et al. |
| 3,866,613 A | 2/1975 | Kenny et al. |
| 3,886,629 A | 6/1975 | Nakai et al. |
| 3,918,452 A | 11/1975 | Cornfield |
| 3,971,378 A | 7/1976 | Krantz |
| 3,983,875 A | 10/1976 | Truman |
| 4,011,034 A | 3/1977 | Curry et al. |
| 4,019,498 A * | 4/1977 | Hawtrey et al. ............... 600/29 |
| 4,060,360 A | 11/1977 | Tapp |
| 4,074,393 A | 2/1978 | Hicklin et al. |
| 4,139,006 A | 2/1979 | Corey |
| 4,144,619 A | 3/1979 | White et al. |
| 4,148,317 A | 4/1979 | Loyer |
| 4,160,004 A | 7/1979 | Curry et al. |
| 4,160,059 A | 7/1979 | Samejima |
| 4,212,301 A | 7/1980 | Johnson |
| 4,261,340 A * | 4/1981 | Baumel et al. ................ 600/32 |
| 4,266,546 A | 5/1981 | Roland et al. |
| 4,307,716 A | 12/1981 | Davis |
| 4,318,407 A | 3/1982 | Woon |
| 4,335,721 A | 6/1982 | Matthews |
| 4,359,357 A | 11/1982 | Friese |
| 4,398,532 A | 8/1983 | Sweeney, III |
| 4,486,191 A | 12/1984 | Jacob |
| 4,494,278 A | 1/1985 | Kroyer et al. |
| 4,498,899 A | 2/1985 | Gross |
| 4,516,570 A | 5/1985 | Taban |
| 4,536,178 A | 8/1985 | Lichstein et al. |
| 4,573,963 A | 3/1986 | Sheldon |
| 4,573,964 A | 3/1986 | Huffman |
| 4,668,557 A | 5/1987 | Lakes |
| 4,669,478 A | 6/1987 | Robertson |
| 4,823,814 A | 4/1989 | Drogendijk et al. |
| 4,857,044 A | 8/1989 | Lennon |
| 4,875,898 A | 10/1989 | Eakin |
| 4,920,986 A | 5/1990 | Biswas |
| 4,921,474 A | 5/1990 | Suzuki et al. |
| 4,973,302 A | 11/1990 | Armour et al. |
| 5,007,894 A | 4/1991 | Enhorning |
| 5,036,867 A | 8/1991 | Biswas |
| 5,041,077 A | 8/1991 | Kulick |
| 5,045,079 A | 9/1991 | West |
| 5,074,855 A | 12/1991 | Rosenbluth et al. |
| 5,080,659 A | 1/1992 | Nakanishi |
| 5,112,348 A | 5/1992 | Glassman |
| 5,147,301 A | 9/1992 | Ruvio |
| 5,224,494 A | 7/1993 | Enhorning |
| 5,273,521 A | 12/1993 | Peiler et al. |
| 5,336,208 A | 8/1994 | Rosenbluth et al. |
| 5,352,182 A | 10/1994 | Kalb et al. |
| 5,355,896 A | 10/1994 | Schulman |
| 5,386,836 A | 2/1995 | Biswas |
| 5,395,308 A | 3/1995 | Fox et al. |
| 5,395,309 A | 3/1995 | Tanaka et al. |
| 5,476,434 A | 12/1995 | Kalb et al. |
| 5,483,976 A | 1/1996 | McLaughlin et al. |
| 5,512,032 A | 4/1996 | Kulisz et al. |
| 5,533,990 A | 7/1996 | Yeo |
| 5,545,179 A * | 8/1996 | Williamson, IV ........... 606/213 |
| 5,554,109 A | 9/1996 | Frayman |
| 5,603,685 A * | 2/1997 | Tutrone, Jr. .................. 600/29 |
| 5,609,559 A | 3/1997 | Weitzner |
| 5,609,586 A | 3/1997 | Zadini et al. |
| 5,611,768 A | 3/1997 | Tutrone, Jr. |
| 5,618,256 A | 4/1997 | Reimer |
| 5,659,934 A | 8/1997 | Jessup et al. |
| 5,752,525 A | 5/1998 | Simon et al. |
| 5,755,906 A | 5/1998 | Achter et al. |
| 5,771,899 A | 6/1998 | Martelly et al. |
| 5,785,640 A | 7/1998 | Kresch et al. |
| 5,795,346 A | 8/1998 | Achter et al. |
| 5,807,372 A | 9/1998 | Balzar |
| 5,813,973 A | 9/1998 | Gloth |
| 5,816,248 A | 10/1998 | Anderson et al. |
| 5,873,971 A | 2/1999 | Balzar |
| 5,885,204 A | 3/1999 | Vergano |
| 5,894,842 A | 4/1999 | Rabin et al. |
| 5,908,379 A | 6/1999 | Schaefer et al. |
| 5,988,169 A | 11/1999 | Anderson et al. |
| 5,988,386 A | 11/1999 | Morrow |
| 6,019,743 A | 2/2000 | Cole et al. |
| 6,030,375 A | 2/2000 | Anderson et al. |
| 6,039,716 A | 3/2000 | Jessup et al. |
| 6,039,828 A | 3/2000 | Achter et al. |
| 6,056,714 A | 5/2000 | McNelis et al. |
| 6,071,259 A | 6/2000 | Steiger et al. |
| 6,090,038 A * | 7/2000 | Zunker et al. ................ 600/29 |
| 6,090,098 A * | 7/2000 | Zunker et al. .............. 604/517 |
| 6,095,998 A | 8/2000 | Osborn, III et al. |
| 6,142,928 A * | 11/2000 | Zunker et al. ................ 600/29 |
| 6,189,535 B1 | 2/2001 | Enhorning |
| 6,248,089 B1 | 6/2001 | Porat |
| 6,270,470 B1 | 8/2001 | Buck et al. |
| 6,283,952 B1 | 9/2001 | Child et al. |
| 6,415,484 B1 | 7/2002 | Moser |
| 6,419,777 B1 | 7/2002 | Achter et al. |
| 6,558,370 B2 * | 5/2003 | Moser ........................ 604/317 |
| 6,645,136 B1 * | 11/2003 | Zunker et al. ................ 600/29 |
| 2002/0083949 A1 | 7/2002 | James |
| 2002/0090390 A1 | 7/2002 | Mahashabde et al. |

FOREIGN PATENT DOCUMENTS

| | | |
|---|---|---|
| WO | WO 96/10965 | 4/1996 |
| WO | WO 98/06365 | 2/1998 |
| WO | WO 98/42281 | 10/1998 |
| WO | WO 00/36996 | 6/2000 |
| WO | WO 00/37013 | 6/2000 |
| WO | WO 02/26173 A2 | 4/2002 |
| WO | WO 02/053071 A1 | 7/2002 |
| WO | WO 02/089704 A2 | 11/2002 |

* cited by examiner

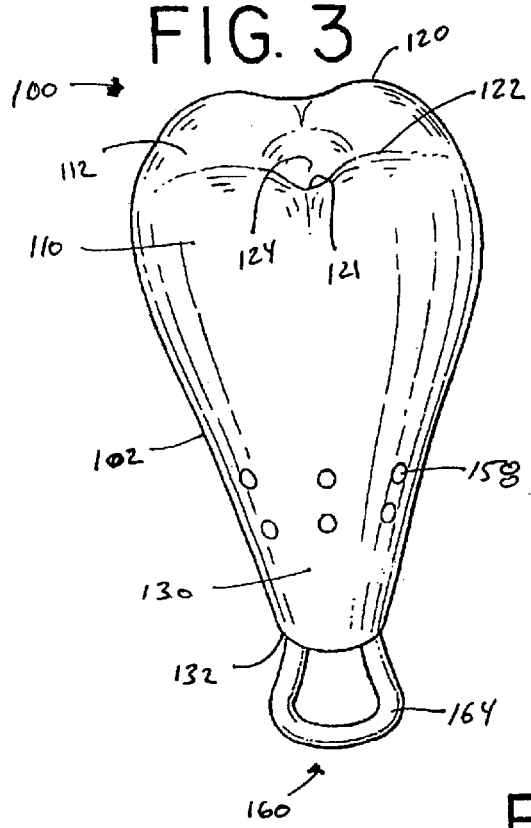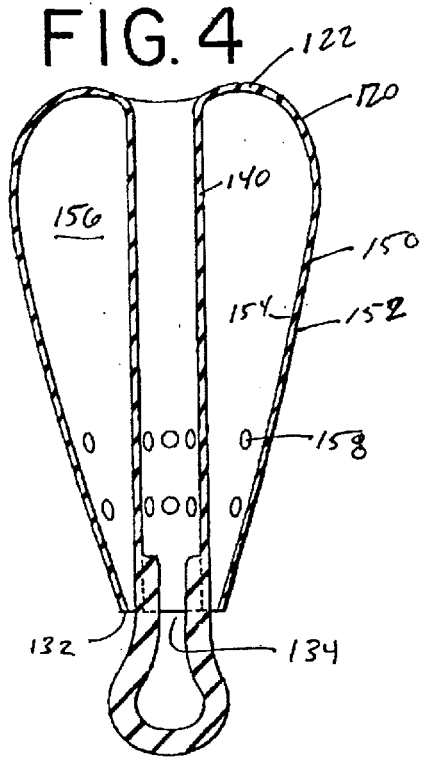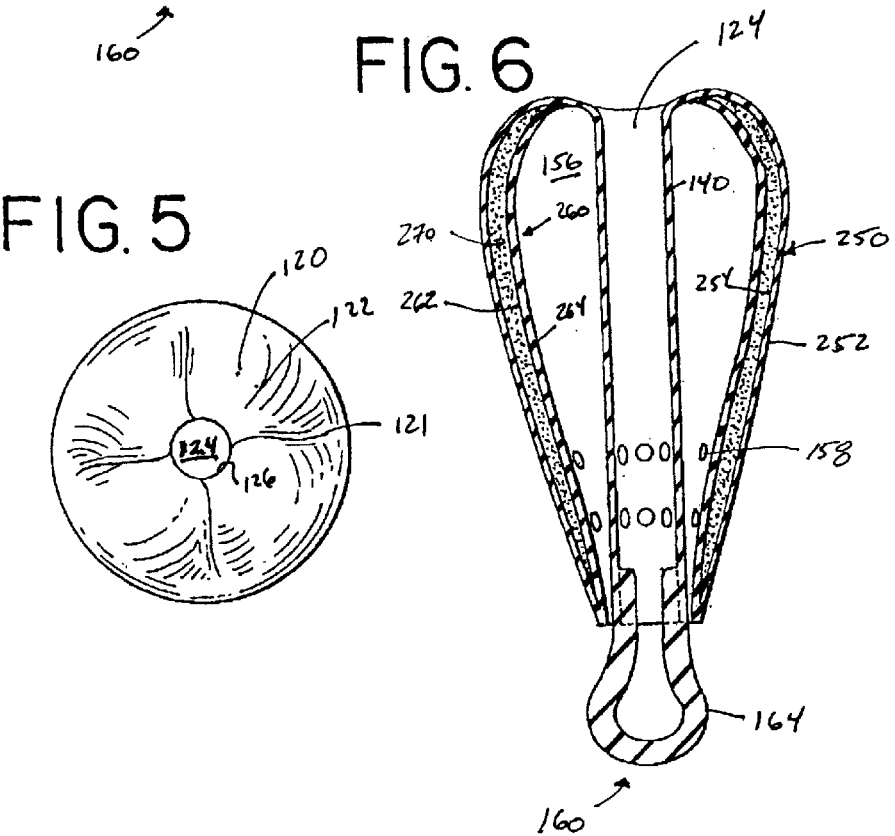

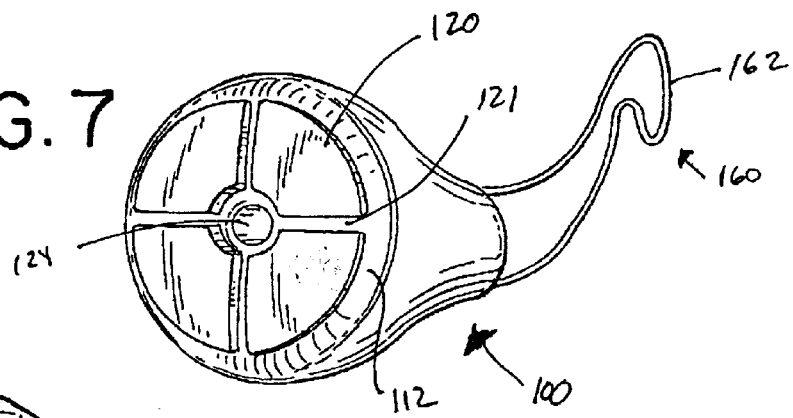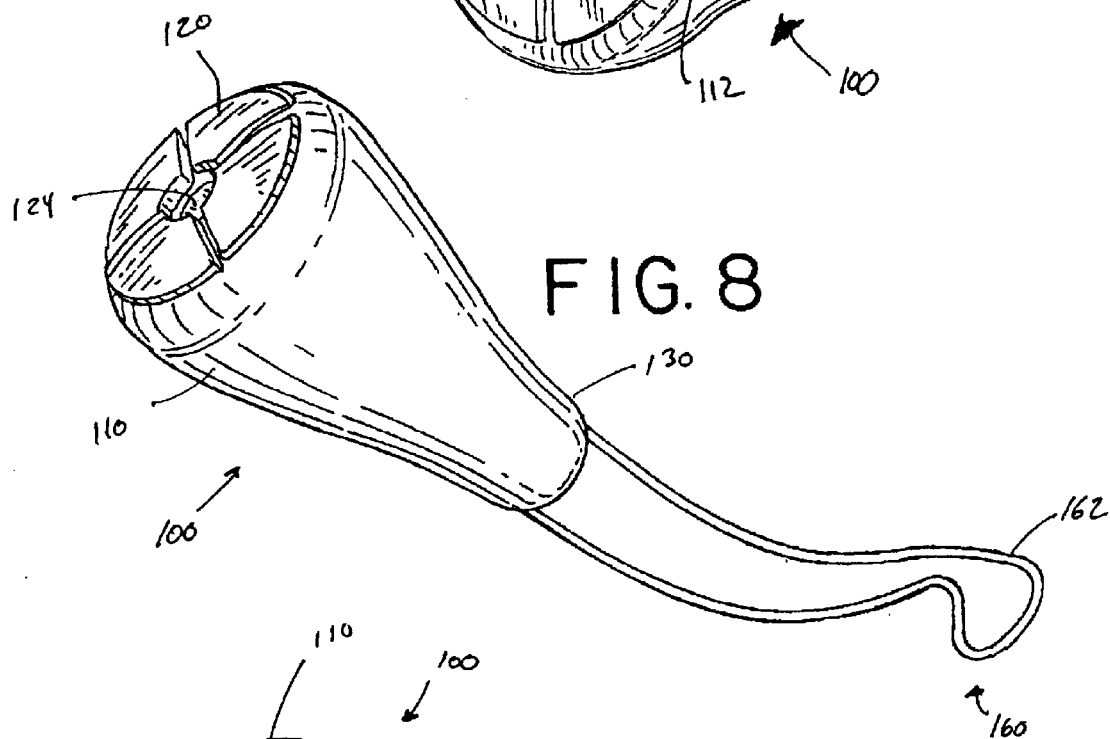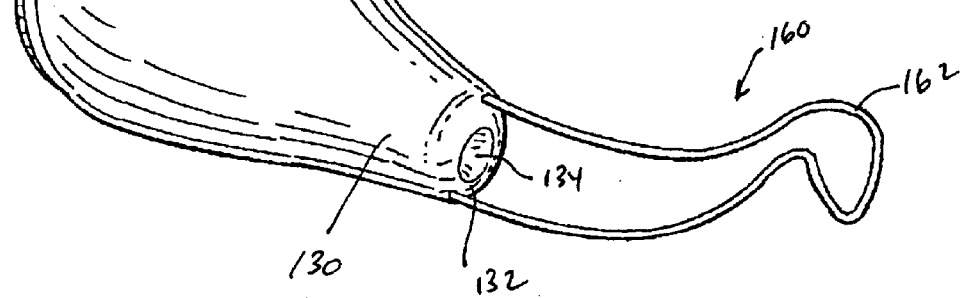

MOLAR SHAPED VAGINAL INCONTINENCE INSERT

FIELD OF THE INVENTION

The present invention relates to a urinary incontinence device and a method of using the same. More specifically, this invention relates to a molar-shaped device for alleviating female urinary incontinence, particularly during episodes of increased intra-abdominal pressure.

BACKGROUND OF THE INVENTION

The primary etiological factor producing genuine stress urinary incontinence is the incomplete transmission of abdominal pressure to the proximal urethra due to displacement from its intra-abdominal position. Some women, especially women who have given birth to one or more children, and older women, can experience incidences of involuntary urine loss due to stress urinary incontinence or combined stress and urge incontinence. A sneeze or cough increases the intra-abdominal pressure which in turn increases the pressure on a person's bladder causing the involuntary release of urine. The frequency and severity of such urine loss can increase as the muscles and tissues near the urethrovaginal myofascial area grow weaker. It has also been recognized that the urinary sphincter muscle, which is located at the upper end of the urethra, adjacent to the bladder, works well at sealing off the passing of urine from the bladder to the urethra when it has a round or circular cross-sectional configuration.

Support of the proximal urethra elevates it above the pelvic floor and subjects it to increases in intra-abdominal pressure, thus allowing compression and maintenance of continence. When this passageway becomes distorted into a cross-sectional configuration having more of an elliptical or oval appearance, however, the sphincter muscle can not close properly. Therefore, the tendency for involuntary urine loss increases. One must remember that the urethra and vagina are not separate structures. Because of their common derivation from the urogenital sinus, they are fused in the distal two-thirds of the urethra. In this region they are bound together by the endopelvic connective tissue so that the support of the urethra depends not only on the attachments of the urethra itself to adjacent structures but also on the connection of the vagina and periurethral tissues to the pelvic wall.

As the world's female population ages, there is an ever-increasing need for a non-surgical method or measure to reduce the involuntary urine loss commonly associated with stress urinary incontinence. Although there are specialized products available for this purpose, most can only be purchased with a prescription and they need to be properly sized, physically inserted and/or adjusted by a medical doctor for them to correctly perform.

In view of the lack of non-prescription, commercially available devices, there is a need for a urinary incontinence device that can be purchased by the consumer and that is uncomplicated and user friendly. Furthermore, there is a need for a urinary incontinence device that is easy for a woman to insert into and remove from their body that is more comfortable to wear and to provide psychological and realistic assurance that it is capable of properly performing over an extended period of time.

SUMMARY OF THE INVENTION

The present invention relates to an intra-vaginal urinary incontinence device that is a molar-shaped resilient insert. The insert may also have a pear shape, tear drop shape, and/or an obconical shape. The insert has a top and a bottom with the cross sectional area of the top being larger than the cross sectional area of the bottom. In use, at least a portion of the top respectively contacts at least the anterior and posterior vaginal walls and may also simultaneously contact the left and right vaginal walls to restore the retropubic position of the bladder neck.

The top of the insert is provided with a top surface that may be closed or may be provided with an aperture. Likewise, the bottom of the insert may be closed or may be provided with an aperture. When an aperture is present on the top surface, an aperture is provided on the bottom surface and the aperture on the top surface communicates with the aperture provided on the bottom surface to allow fluids to pass through the insert. In one embodiment, a channel is provided to connect the aperture provided on the top surface with the aperture provided on the bottom surface.

In a particular embodiment, the top surface of the insert includes at least one cusp that extends upward from the top surface to define an area of greater resistance to deformation as compared to an area that does not contain a cusp. The top surface may include at least two opposed cusps and, in one embodiment, may include three cusps in a triangular formation. Alternatively, the top surface may include four cusps, with each cusp being both diagonally and laterally opposed to another cusp. In this embodiment, the aperture may be centrally located between each cusp.

In use, the area adjacent the at least two opposed cusps will contact the anterior and posterior vaginal walls such that the urethra will rest in the area between the cusps. As a result, the bladder neck will be restored to a more normal retropubic position and the urethra will be properly aligned with the bladder neck thereby restoring continence.

The insert may also be provided with a removal member that cooperates with the insert to allow the insert to be removed from the vagina. The removal member may be separate from or integral with the insert. Accordingly, in one embodiment, the removal member is attached to at least a portion of the bottom of the insert. In another embodiment, the removal member is attached to the channel that connects the top and bottom apertures.

The insert may be formed from a variety of biocompatible materials and may be formed as a solid or semi-solid mass of a compressible, resilient, biocompatible material. Alternatively, the insert may be formed such that the insert has a thin wall that defines an outer surface and an inner surface. In this embodiment, the inner surface defines an interior of the insert. The interior may contain a resilient material that allows the wall of the insert to deform and conform to the shape of the object acting to deform the wall such as one or more of the vaginal walls.

Put another way, the device of the present invention is an intra-vaginal device that can simultaneously engage the anterior vaginal wall and the posterior vaginal wall, or each of the anterior vaginal wall, the posterior vaginal wall, the left vaginal wall and the right vaginal wall. The cusps provide anatomical realignment of the urethra and sphincter muscles to restore the retropubic position of the bladder neck so intra-abdominal pressure is once again transmitted equally to the bladder and urethra. The device is formed of a resilient material so that, in use, it may be resiliently deformed to conform to the shape of the vaginal walls.

The present invention also includes a method of alleviating female urinary incontinence by providing a female urinary incontinence device as described above and in the specification below, selectively inserting the device into a woman's vagina so that the device simultaneously contacts or the anterior vaginal wall and the posterior vaginal wall or all the walls in the bladder neck region to restore the retropubic position of the bladder neck.

Advantageously, the device and method of present invention provides for control of female urinary incontinence by use of a device that does not create undue friction or distension of the mucosal tissue and yet allows for normal discharge of vaginal secretions.

BRIEF DESCRIPTION OF THE DRAWINGS

FIG. 3 is a perspective view of one embodiment of the urinary incontinence device of the present invention.

FIG. 4 is a longitudinal sectional view of the embodiment of FIG. 3.

FIG. 5 is a top view of the urinary device shown in FIG. 3.

FIG. 6 is a cut-away view of one embodiment of the urinary device of the present invention that shows the wall forming the device filled with a resilient material.

FIG. 7 is a top perspective view of another embodiment of the urinary incontinence device of the present invention.

FIG. 8 is a perspective view of the urinary incontinence device of FIG. 7.

FIG. 9 is a rear perspective view of the urinary incontinence device of FIG. 7.

DESCRIPTION OF THE INVENTION

Figure 1:
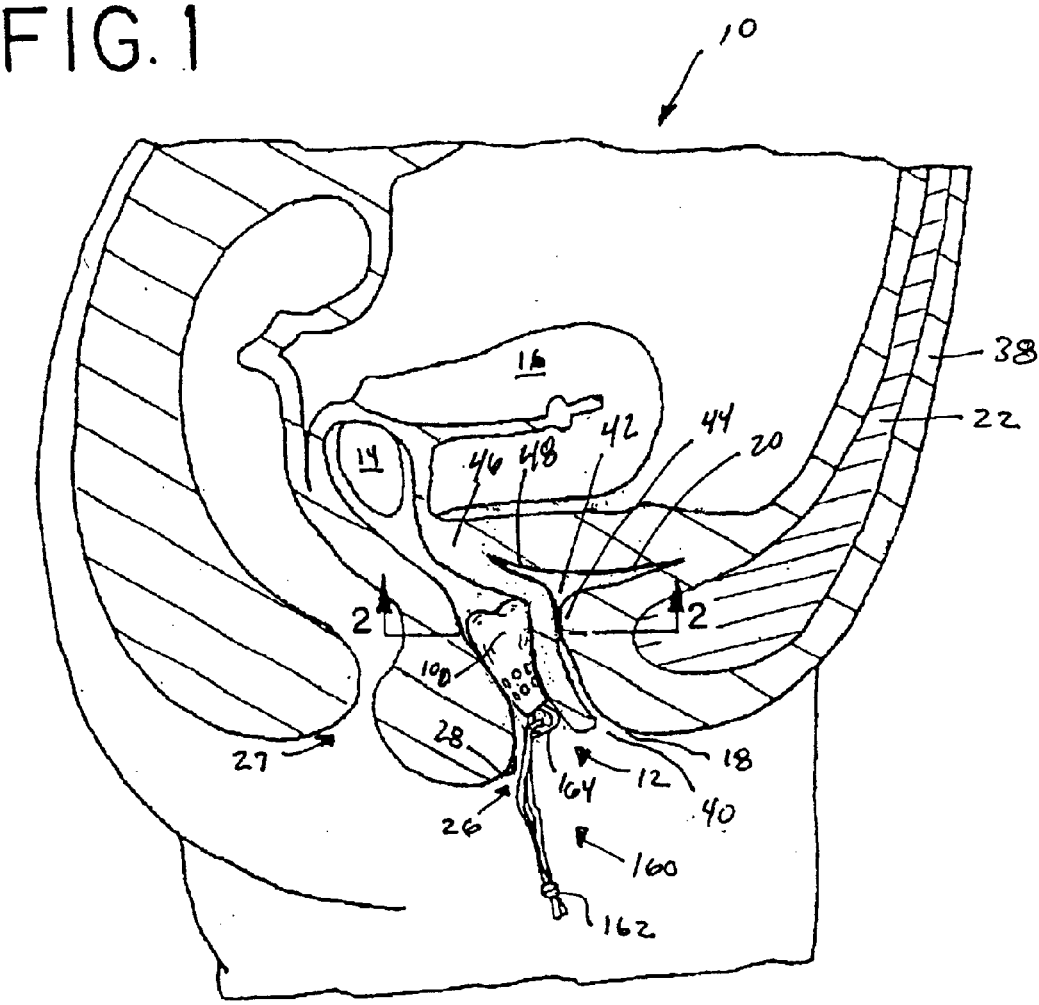
FIG. 1 is a mid-sagittal section of a human torso showing one embodiment of a urinary incontinence device positioned in the vaginal canal showing the cusps of the device aligned with the bladder neck region to elevate and support the bladder and to cooperate with the symphysis pubis to allow the urethral tube to be compressed upon itself and alleviate urinary incontinence during episodes of increased intra-abdominal pressure.

Turning now to FIG. 1, a human torso 10 of a female is shown with a vagina 12, a cervix 14, a uterus 16, a urethra 18, a bladder 20 and a symphysis pubis 22. The vagina 12 has an introital opening 24 that exits the human body 10 and contains a vaginal canal 26 that extends from the introital opening 24 to the cervix 14. The vaginal canal 26 has a length that ranges from between about 4 inches to about 6 inches (about 102 millimeters (mm), to about 153 mm) in most women. The cervix 14 is the entrance to the womb and is located between the upper aspect of the vaginal canal 26 and the uterus 16. The rectum 27 is located posterior to the vagina 12. The vaginal canal 26 has an inner periphery 28.

Figure 2:
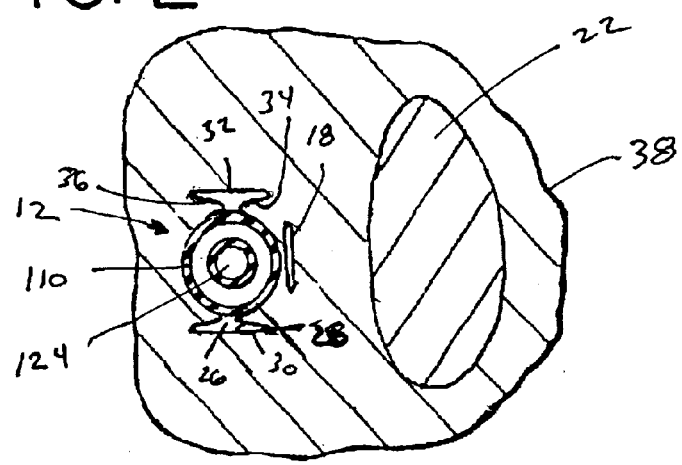
FIG. 2 is a sectional view taken along line 2—2 of FIG. 1 wherein the device circumferentially contacts the anterior vaginal wall and the posterior vaginal wall.

As best seen in FIG. 2, the inner periphery 28 is made up of a right lateral wall 30, a left lateral wall 32, an anterior wall 34, and a posterior wall 36. The four walls 30, 32, 34, and 36 encompass the entire 360 degrees of the inner periphery 28. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is the most important section for alleviating female urinary incontinence because of its proximity to the urethra 18 and is the location where a urinary incontinence device should be positioned. The middle third of the vaginal canal 26 is also horizontally offset from the symphysis pubis 22, which is a bony prominence situated adjacent to a front portion 38 of the human torso 10 and may be referred to the bladder neck region 50. Cooperation between a urinary incontinence device positioned in the vagina 12 and the symphysis pubis 22 allows the urethra 18 to be compressed upon itself thereby providing a means to alleviate involuntary urine flow from the bladder.

The urethra 18, also referred to as a urethral tube, is a hollow tubular structure that extends from a first opening 40 that exits the human body 10 to a second opening 42 situated at the lower surface of the bladder 20. The urethra 18 has a length of about 1.5 inches (about 38 mm) in most women. The urethra functions to discharge urine, which is temporarily stored in the bladder 20, from the human body. The urethra 18 has a plurality of urethral sphincter muscles 44 located along the length of its inner periphery. The urethral sphincter muscles 44 are situated below the opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIG. 1, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) which transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

A urinary incontinence device 100 is shown positioned in the vaginal canal 26 and, in particular, in the bladder neck region 50. The urinary incontinence device 100 is designed to bridge across the vagina to support the musculature and body tissue located in the urethra-vaginal myofascial area 46. In other words, the device 100 and, in particular, the at least one cusp 120 elevates the bladder neck 50 to a more normal retropubic position thereby restoring continence.

In FIG. 2, the urinary incontinence device 100 is shown in use. A portion of the urinary incontinence device 100 and, in particular, a portion of the top 110 of the insert 102 is directly touching the anterior and posterior walls 34 and 36. Alternatively, the insert 102 can be selectively positioned such that a portion of the top 110 can be touching both the right and left lateral walls 30, 32 and the anterior and posterior walls 34, 36 to provide a supportive backdrop for the urethral tube 18 and to support the bladder neck region 50 thereby restoring continence. The urethral tube 18 will now be sufficiently compressed to intercept the flow of urine and to provide support to the urinary sphincter muscle 44 so that it can function properly. By permitting the urethral tube 18 to be compressed upon itself between the urinary incontinence device 100 and the symphysis pubis 22, the involuntary flow of urine from the bladder is limited.

Referring now to FIG. 3, a perspective view of one embodiment of the device 100 of the present invention is shown. The device is a molar shaped insert 102 with a top 110 and a bottom 130. As used in the specification and claims, the top of the insert 110 refers to that portion of the insert 102 that is first inserted into the vagina. While the insert 102 is described as being molar shaped, it may also be shaped in the form of a pear, a tear drop, an obconical, or similar shape. Accordingly, the term "molarshaped" is meant to include a shape as depicted in FIGS. 3 and 7–9, as well as a pear shape, a tear drop shape, an obconical, or similar shape.

Common to each of these shapes is that the top of the insert 110 has a cross-sectional area that is greater than the cross-sectional area of the bottom of the insert 130. In addition, it is preferred that the shape of the insert 102 does not present any sharp corners or surfaces but instead is shaped to present rounded or curved surfaces to minimize any discomfort during insertion, use, and removal of the device 100. Accordingly, in the embodiment shown in FIG. 3, the top 110 and bottom 130 have a round cross-section and, in particular, a substantially circular cross-section. Alternatively, the top 110 and bottom 130 may have an oblong or elliptical cross section.

As best in FIGS. 4, 5, and 7, the top of the insert 110 has a top surface 112 that includes at least one cusp 120 that extends upward from the top surface 112 an amount not less than about 5 mm but not more than about 30 mm. Preferably, the cusp extends upward from the top surface from about 5 mm to about 30 mm, more preferably about 10 mm. As shown in FIGS. 3 and 5, the top surface of the cusp 122 may be rounded to minimize any discomfort during insertion, use, and removal of the device.

Alternatively, as shown in FIGS. 7 and 8, the cusps 120 may have a top surface 122 that is substantially flat. In this embodiment, the cusps 120 are sector-shaped with the portion of the cusp 120 adjacent the aperture 124 being rounded and extending from the top surface 112 a distance greater than the portion of the cusp 120 adjacent the outer edge of the insert 102. Alternatively, the cusp 120 may extend an equal distance from the top surface 112, if desired. In addition, four cusps 120 are shown and are spaced from each other to define a valley 121.

The cusp 120 defines an area of the top of the insert 110 that exhibits a greater resistance to deformation as compared to an area of the top of the insert 110 that does not include a cusp. Desirably, the insert 102 is selectively positioned so that the portion of the top of the insert 110 adjacent the portion of the top surface 112 that includes a cusp 120 to support the bladder neck region 50.

In one embodiment, the top surface of the insert 110 is provided with at least two cusps 120 with each cusp 120 being opposite another cusp 120. In another embodiment, three cusps 120 are provided in a triangular arrangement. In a preferred embodiment, the top surface 110 is provided with four cusps 120, with each cusp 120 being diagonally and laterally opposed to another cusp 120. In this preferred embodiment, therefore, the cusps 120 define four areas of the top of the insert 110 that exhibit greater resistance to deformation as compared to the area of the top of the insert 110 that does not contain a cusp 120. In addition, when four cusps 120 are provided, adjacent cusps 120 define a corresponding valley 121 located between the adjacent cusps 120.

Advantageously, when four cusps 120 are provided, the insert 102 will always assume the correct position. Accordingly, the insert 102 is selectively positioned so that the portion of the top of the insert 110 adjacent each cusp 120 is in contact with at least the anterior and posterior vaginal wall 34, 36 to elevate and support the bladder neck 50. In addition, when the insert 102 is positioned within the vagina, the valley 121 will desirably keep the urethra 18 properly aligned with the bladder neck 50.

The top of the insert 110 also has a top surface 112 that may be completely closed or, as best seen in FIGS. 4 and 5, may have an aperture 124. Likewise, the bottom 130 has a bottom surface 132 that may be completely closed or, as best seen in FIG. 5, may have an aperture 134. Where the top surface 112 is provided with an aperture 124, an aperture 134 is likewise provided on the bottom surface 132 so that the aperture on the top surface 124 communicates with the aperture on the bottom surface 134, to allow normal discharge of vaginal secretions. Desirably, the top aperture 124 is provided in a centrally located position on the top surface of the insert 112. Accordingly, when the insert 102 is provided with four cusps 120, the top aperture 124 is centrally located between each of the cusps 120.

In a preferred embodiment as shown in FIG. 4, a channel 140 is provided to connect the top aperture 124 with the bottom aperture 134 to facilitate the transport of any fluids entering the top aperture 124, through the insert 102, and out the bottom aperture 134. More preferably, the channel 140 defines the outer periphery of the top aperture 126 and the channel 140 extends downward through the insert 102 and terminates adjacent the bottom aperture 134.

Referring to FIG. 4, the insert 102 is shown as formed of a thin wall 150 to define an outer surface 152 and an inner surface 154 where the inner surface 154 defines an interior of the insert 156. The thin wall 150 may have a thickness from about 0.025 mm to about 10 mm, preferably from about 1 mm to about 7 mm, more preferably about 2 mm. When the insert 102 is formed of a thin wall 150, the insert 102 may be molded as a single piece such that the channel 140 described above is integral with the aperture on the top surface 124.

The interior of the insert 154 may be filled with a resilient material that allows the wall 150 and thus the insert 102 to conform to the shape of an object deforming the wall 150. The resilient material may include but is not limited to biocompatible fluids, mineral oil, silicone, saline, gels, clay, rubber, wool, fibrous material, semi-solid materials, and mixtures thereof.

Alternatively, the interior 156 may not be filled with a resilient material. In this case, at least one vent 158 and preferably a plurality of vents 158 may be provided on the thin wall 150 to aid in insertion and removal of the insert 102. The vents may be located adjacent the top 110, the bottom 130, or may cover the entire surface.

Referring now to FIG. 6, another embodiment of the present invention is shown where like reference numerals designate the same or similar parts as those shown in the other figures. In this embodiment, the thin wall 150 forming the insert 102 is a double wall structure that includes an outer wall 250 and an inner wall 260. The outer wall 250 defines an outer surface 252 and an inner surface 254. Likewise, the inner wall 260 defines an outer surface 262 and an inner surface 264. Together, the inner surface 254 and the outer surface 262 define a plenum 270.

The plenum 270 may be filled with air or other suitable gas or may be filled with a resilient material that will allow the thin wall 150 and the outer wall 250 and inner wall 260 to conform to the shape of an object contacting and deforming the outer surface 252 of the outer wall 250. The resilient material may include but is not limited to biocompatible fluids, mineral oil, silicone, saline, gels, clay, rubber, wool, fibrous material, semi-solid materials, and mixtures thereof.

The device 100 may also be provided with a removal member 160 to facilitate the removal of the insert 102. The removal member 160 may be separate from the insert 102 or may be integrally formed with the insert 102. When the removal member 160 is integrally formed with the insert 102, pulling on the removal member 160 will cause the insert 102 to inwardly collapse upon itself to reduce the cross-sectional area of the top 110 of the insert for easier removal. Preferably, the removal member 160 is connected to a portion of the bottom of the insert 130. The removal member 160 has a shape suitable to be grasped so that the insert 102 may be removed. For example, FIGS. 1–4 show the removal member 160 as a ring 164 and FIGS. 7–9 show the removal member 160 as a string 162.

Again referring to the embodiment shown in FIG. 4, the removal member 160 is shown as integrally formed with the channel 140 so that as the removal member 160 is pulled downward (i.e., in a direction from the top toward the bottom of the insert), the top of the insert 110 is urged downward to follow the bottom of the insert 130 out the vagina. In this embodiment, when the removal member 160 is integrally formed with the insert 102 and, in particular the channel 140, pulling on the removal member 160 will cause the insert 102 to inwardly collapse upon itself to reduce the cross-sectional area of the top 110 of the insert for easier removal.

The device 100 not including the removal member may have a length from about 10 mm to about 120 mm, preferably from about 30 mm to about 90 mm, more preferably from about 50 mm to about 70 mm and most preferably about 65 mm. The top of the device may also have a cross-sectional area from about 10 mm to about 70 mm, preferably from about 30 mm to about 60 mm, and most preferably about 38 mm.

Advantageously, the device 100 may be of a unitary construction and may be formed by molding an inert, biocompatible synthetic resin that has a modulus of elasticity. One such resin is a molded silicone compound, polyurethane, or other suitable biocompatible material or a combination of materials. As noted above, the device 100 may be formed of a solid or semi-sold resilient mass or may be formed with a thin wall 150 as described with respect to FIGS. 1–5. In any event, the device 100 whether made of unitary construction or otherwise, is made of a suitable biocompatible material, which is known to those of skill in the art. The device 100 may be covered with a suitable biocompatible outer cover material.

The device of the present invention as described above may be disposed after a single use, may be worn more than once, or may be reusable for a period of time (e.g., one week) before being disposed.

In accordance with another aspect of the invention, a method of instructing a consumer is provided. In this aspect, the method includes providing a molar-shaped insert to a user for alleviating female urinary incontinence and comprises the steps of providing a molar-shaped insert comprising a top having a first cross sectional area and a bottom having a second cross sectional area, wherein the first cross sectional area is greater than the second cross section area; and instructing the user to place the insert into a woman's vagina, wherein at least a portion of the top of the insert contacts an anterior vaginal wall and a posterior vaginal wall.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. A vaginal urinary incontinence device comprising a flexible molar-shaped insert having a top and a bottom wherein the top has a cross-sectional area greater than a cross-sectional area of the bottom and wherein the top has a surface that includes at least two opposed cusps, wherein the cusps provide a degree of resistance to deformation greater than the portion of the surface that does not include the cusps such that when the insert is inserted within a vagina, at least a portion of the top contacts an anterior vaginal wall and a posterior vaginal wall.

2. The device of claim 1 wherein the top has a substantially circular cross section.

3. The device of claim 1 wherein the top has a top surface with an aperture that communicates with an aperture provided on the bottom.

4. The device of claim 3 comprising a channel connecting the aperture provided on the top surface to the aperture provided on the bottom wherein fluids entering the aperture on the top surface are transported through the device and out the aperture provided on the bottom.

5. The device of claim 4 further comprising a removal member located adjacent the bottom.

6. The device of claim 5 wherein the removal member is attached to at least a portion of the channel.

7. The device of claim 1 wherein the top has a surface that includes four cusps, with each cusp being both diagonally and laterally opposed to another cusp.

8. The device of claim 6 further comprising a centrally located aperture provided on the top surface and communicating with an aperture provided on the bottom.

9. The device of claim 1 further comprising a removal member located adjacent the bottom.

10. The device of claim 1 further comprising at least one vent provided on the molar-shaped insert.

11. The device of claim 1 wherein the molar-shaped insert has a thin wall to define an outer surface and an inner surface.

12. The device of claim 11 wherein the inner surface defines an interior of the insert.

13. The device of claim 12 further comprising a resilient material within the interior of the molar-shaped insert to allow the wall to conform to a shape of an object deforming the wall.

14. The device of claim 11 wherein the thin wall is formed with an outer wall and an inner wall spaced from the outer wall to define a plenum.

15. The device of claim 1 wherein the molar-shaped insert is a solid mass of compressible resilient material.

16. A method of providing a molar-shaped insert to a user for alleviating female urinary incontinence comprising the steps of:

a. providing a molar-shaped insert comprising a top having a first cross sectional area and a bottom having a second cross sectional area, wherein the first cross sectional area is greater than the second cross section area and wherein the top has a surface that includes at least two opposed cusps, wherein the cusps provide a degree of resistance to deformation greater than the portion of the surface that does not include the cusps; and b. instructing the user to place the insert into a woman's vagina, wherein at least a portion of the top of the insert contacts an anterior vaginal wall and a posterior vaginal wall.

17. The method of claim 16 further comprising removing the device from the vagina.

* * * * *